US012605368B2

(12) United States Patent
Hagiwara et al.

(10) Patent No.: US 12,605,368 B2
(45) Date of Patent: Apr. 21, 2026

(54) SUPPRESSION OF NEUROINFLAMMATION AND COMPOSITION AND METHOD THEREFOR

(71) Applicant: Kyoto University, Kyoto (JP)

(72) Inventors: Masatoshi Hagiwara, Kyoto (JP); Akiko Kobayashi, Kyoto (JP)

(73) Assignee: Kyoto University, Kyoto (JP)

( * ) Notice: Subject to any disclaimer, the term of this patent is extended or adjusted under 35 U.S.C. 154(b) by 711 days.

(21) Appl. No.: 17/915,751

(22) PCT Filed: Mar. 31, 2021

(86) PCT No.: PCT/JP2021/014030
§ 371 (c)(1),
(2) Date: Sep. 29, 2022

(87) PCT Pub. No.: WO2021/201171
PCT Pub. Date: Oct. 7, 2021

(65) Prior Publication Data

US 2023/0117374 A1 Apr. 20, 2023

(30) Foreign Application Priority Data

Apr. 1, 2020 (JP) ................................ 2020-066150

(51) Int. Cl.

| | |
|---|---|
| ***A61K 31/4439*** | (2006.01) |
| ***A61K 31/428*** | (2006.01) |
| ***A61K 31/429*** | (2006.01) |
| ***A61P 25/00*** | (2006.01) |

(52) U.S. Cl.
CPC ........ *A61K 31/429* (2013.01); *A61K 31/4439* (2013.01); *A61P 25/00* (2018.01)

(58) Field of Classification Search
CPC ... A61K 31/4439; A61K 31/428; A61P 25/00; A61P 25/28; A61P 29/00
USPC ................................................ 514/338, 366
See application file for complete search history.

(56) References Cited

U.S. PATENT DOCUMENTS

| | | | | |
|---|---|---|---|---|
| 9,745,323 | B2 * | 8/2017 | Hagiwara | A61P 25/00 |
| 11,318,126 | B2 * | 5/2022 | Hagiwara | A61P 9/10 |
| 2015/0266825 | A1 | 9/2015 | Hood et al. | |
| 2016/0106719 | A1 | 4/2016 | Takahashi | |
| 2016/0303089 | A1 | 10/2016 | Hagiwara et al. | |
| 2017/0355715 | A1 | 12/2017 | Hagiwara et al. | |
| 2019/0119263 | A1 | 4/2019 | Kc et al. | |
| 2019/0247384 | A1 | 8/2019 | Hagiwara et al. | |

FOREIGN PATENT DOCUMENTS

| | | | |
|---|---|---|---|
| EP | 2881397 | A1 | 6/2015 |
| EP | 3508223 | A1 | 7/2019 |
| JP | 2018-076385 | A | 5/2018 |
| WO | 2015/083750 | A1 | 6/2015 |
| WO | 2015/143380 | A1 | 9/2015 |
| WO | 2018/029793 | A1 | 2/2018 |
| WO | 2018/043674 | A1 | 3/2018 |
| WO | 2019/079626 | A1 | 4/2019 |

OTHER PUBLICATIONS

Extended European Search Report issued in European Patent Application No. 21779632.5 dated Jul. 4, 2024.
Tomov, "Glial cells in intracerebral transplantation for Parkinson's disease," Neural Regeneration Research, 15 (7): 1173-1178 (2020).
Grade et al., "Neuronal replacement therapy: previous achievements and challenges ahead," NPJ Regenerative Medicine, 2 (1) (2017).
Zhang et al., "Neural stem cell transplantation therapy for brain ischemic stroke: Review and perspective," World Journal of Stem Cells, 11 (10): 817-830 (2019).
Dooley et al., "Immunopharmacological intervention for successful neural stem cell therapy: New perspectives in CNS neurogenesis and repair," Pharmacology & Therapeutics, 141: 21-31 (2014).
Ogawa et al., "Development of a novel selective inhibitor of the Down syndrome-related kinase Dyrk1A," Nature Communications, 1: 86 (2010).
Woo et al., "The novel DYRK1A inhibitor KD03 alters neuroinflammation in BV2 microglial cells, wild-type, and Alzheimer's transgenic mice," IBRO Reports, 6: S130 (2019).
Melchior et al., "Anti-Inflammatory Effects of SM07883, A Novel, Potent, and Selective Oral DYRK1A Inhibitor in Neurodegenerative Mouse Models," Alzheimer's and Dementia, 15 (7): P216 (2019).
Sun et al., "Dyrk2 involved in regulating LPS-induced neuronal apoptosis," International Journal of Biological Macromolecules, 104: 979-986 (2017).
Lee et al., The novel DYRK1A inhibitor KNV93 regulates cognitive function, amyloid-beta pathology, and neuroinflammation, Free Radical Biology and Medicine, 160: 575-595 (2020).
"Stem cell therapy for stroke using iPS cells," Nippon Rinsho, 72 (Suppl.5) 453-458 (2014) (see partial English translation).
Nakamura et al., "Transplantation of neural stem cells into spinal cord injury," Nippon Rinsho, 61 (3): 463-468 (2003) (see partial English translation).

(Continued)

*Primary Examiner* — Charanjit Aulakh
(74) *Attorney, Agent, or Firm* — Morgan, Lewis & Bockius LLP

(57) ABSTRACT

A pharmaceutical composition for suppressing neuro-inflammation; a pharmaceutical composition for assisting transplantation of neuron precursor cells, pluripotent stem cells, and/or neurons; a pharmaceutical composition for promoting the stabilization of Nrf2 protein in glial cells; a pharmaceutical composition for protecting nerve cells from neuro-inflammation are provided. Provided is a pharmaceutical composition containing, as an active ingredient, a compound having an inhibiting ability against phosphorylation activity of DYRK1A protein, or a pharmaceutically acceptable salt of the compound.

18 Claims, 9 Drawing Sheets

(56) References Cited

OTHER PUBLICATIONS

Nakano-Kobayashi et al., Therapeutics potentiating microglial p21-Nrf2 axis can rescue neurodegeneration caused by neuroinflammation, Science Advances, 6: eabc1428 (2020).

Partial Supplementary European Search Report issued in European Patent Application No. 21779632.5 dated Mar. 18, 2024.

Souchet et al., "Inhibition of DYRK1A proteolysis modifies its kinase specificity and rescues Alzheimer Phenotype in APP/PS1 mice," Acta Neuropathologica Communications, 7 (1): 46 (2019).

Melchior et al., "Tau pathology reduction with SM07883, a novel, potent, and selective oral DYRK1A inhibitor: A potential therapeutic for Alzheimer's disease," Aging Cell, 18 (5): e13000 (2019).

* cited by examiner

SUPPRESSION OF NEUROINFLAMMATION AND COMPOSITION AND METHOD THEREFOR

TECHNICAL FIELD

The present disclosure relates to suppression of neuro-inflammation, as well as a composition and a method for suppressing neuro-inflammation. In one or a plurality of aspects, the present disclosure relates to assistance of transplantation of neuron precursor cells, pluripotent stem cells, and/or neurons, as well as a composition and a method for the same. In one or a plurality of aspects, the present disclosure relates to promotion of stabilization of NF-E2-related factor 2 (Nrf2) protein in glial cells, as well as a composition and a method for the same. In one or a plurality of aspects, the present disclosure relates to protection of nerve cells from neuro-inflammation, as well as a composition and a method for the same.

BACKGROUND ART

Parkinson's disease is a progressive neurodegenerative disease, and is characterized by loss of nigrostriatal dopaminergic nerves (dopaminergic neurons). The past clinical researches have proven that transplantation of embryonic mesencephalic cells improves motion symptoms of Parkinson's disease patients. Based on such facts, cell replacement therapy is suggested as a method for treating Parkinson's disease.

Pluripotent stem cells, particularly, induced pluripotent stem cells (iPS cells, or iPSC), have possibility of supplying a great deal of dopaminergic nerves. Pluripotent stem cells are therefore considered a new donor cell source. Neuron precursor cells and dopaminergic nerve cells differentiated from stem cells such as iPS cells, however, exhibit an extremely low retention rate (survival rate) after intracerebral transplantation (Patent Document 1).

Microglia is a type of glial cells that exist in the central nervous system (the brain and the spinal cord). Microglia is also called microgliacyte or Hortega cell.

Microglia is considered to be an immunocompetent cell such as macrophage. Microglia has a variety of activities and roles such as an antigen-presenting activity of serving as a starting point of an immunological reaction, an innate immunity activity against a foreign substance, phagocytosis with respect to foreign substances and wastes, assistance for the formation of a neural circuit, and production of various types of substances to influence surrounding cells.

Microglia, responding to external stimulus, stress, or the like, shifts to an active state, and produces useful substances such as antioxidant substances and neurotrophic factors. Microglia, however, upon pathological activation, secretes proinflammatory cytokine, chemokine, nucleic acid, excitatory amino acid such as or glutamic acid, active oxygen species, protease, etc., and damages surrounding cells, thereby serving as a starting point of neuro-inflammation. Microglia thus can cause neurodegeneration of the central nervous system (Patent Document 2).

A compound that has an inhibiting ability against phosphorylation activity of DYRK1A protein as a protein phosphorylation enzyme has been reported to be effective for neurogenesis or nerve cell growth (Patent Documents 3 and 4). DYRK, standing for dual specificity tyrosine-phosphorylation-regulated kinase, is the general term for these enzymes.

PRIOR ART DOCUMENT

Patent Document

[Patent Document 1] JP-A-2018-76385
[Patent Document 2] WO2018/029793
[Patent Document 3] WO2015/083750
[Patent Document 4] WO2018/043674

SUMMARY OF THE INVENTION

Problem to be Solved by the Invention

The present disclosure, in one aspect, provides a pharmaceutical composition for suppressing neuro-inflammation.

The present disclosure, in one aspect, provides a pharmaceutical composition for assisting transplantation of neuron precursor cells, pluripotent stem cells, and/or neurons.

The present disclosure, in one aspect, provides a pharmaceutical composition for promoting the stabilization of Nrf2 protein in glial cells.

The present disclosure, in one aspect, provides a pharmaceutical composition for protecting nerve cells from neuro-inflammation.

Means to Solve the Problem

The present disclosure, in one aspect, relates to a pharmaceutical composition for suppressing neuro-inflammation, the pharmaceutical composition containing, as an active ingredient, a compound having an inhibiting ability against phosphorylation activity of DYRK1A protein, or a pharmaceutically acceptable salt of the compound.

The present disclosure, in another aspect, relates to a pharmaceutical composition for assisting transplantation of neuron precursor cells, pluripotent stem cells, and/or neurons, the pharmaceutical composition containing, as an active ingredient, a compound having an inhibiting ability against phosphorylation activity of DYRK1A protein, or a pharmaceutically acceptable salt of the compound.

The present disclosure, in another aspect, relates to a pharmaceutical composition for promoting the stabilization of Nrf2 protein in glial cells, the pharmaceutical composition containing, as an active ingredient, a compound having an inhibiting ability against phosphorylation activity of DYRK1A protein, or a pharmaceutically acceptable salt of the compound.

The present disclosure, in another aspect, relates to a pharmaceutical composition for protecting nerve cells from neuro-inflammation, the pharmaceutical composition containing, as an active ingredient, a compound having an inhibiting ability against phosphorylation activity of DYRK1A protein, or a pharmaceutically acceptable salt of the compound.

The present disclosure, in another aspect, relates to a method for suppressing neuro-inflammation, the method including administering, to a subject, an effective amount of the pharmaceutical composition according to the present disclosure.

The present disclosure, in another aspect, relates to a method for increasing a survival rate of transplanted neuron precursor cells, pluripotent stem cells, and/or neurons, the method including administering, to a recipient, an effective amount of the pharmaceutical composition according to the present disclosure before, simultaneously with, or after transplantation of the neuron precursor cells, pluripotent stem cells, and/or neurons.

The present disclosure, in another aspect, relates to a method for promoting the stabilization of Nrf2 protein in glial cells and protecting nerve cells from neuro-inflammation, the method including administering, to a subject, an effective amount of the pharmaceutical composition according to the present disclosure.

The present disclosure, in another aspect, relates to a method for ameliorating, suppressing progression of, and/or treating a disease accompanied by neuro-inflammation selected from the group consisting of frontotemporal lobar degeneration, amyotrophic lateral sclerosis, and multiple sclerosis, the method including administering, to a subject, an effective amount of the pharmaceutical composition according to the present disclosure.

Effect of the Invention

In one or a plurality of embodiments, the pharmaceutical composition according to the present disclosure is capable of suppressing neuro-inflammation.

In one or a plurality of embodiments, the pharmaceutical composition according to the present disclosure is capable of enhancing the post-transplantation survival rate of neuron precursor cells, stem cells, and/or neurons transplanted.

In one or a plurality of embodiments, the pharmaceutical composition according to the present disclosure is capable of promoting and enhancing the stabilization of Nrf2 protein in glial cells.

In one or a plurality of embodiments, the pharmaceutical composition according to the present disclosure is capable of protecting nerve cells from neuro-inflammation.

BRIEF DESCRIPTION OF DRAWINGS

FIG. 1A shows results of Western blotting analyses on microglial cells treated with a compound 1. FIG. 1B shows representative images of glial cells treated with the compounds 1 and 2. FIG. 1C shows exemplary quantification of signal intensities of Nrf2 in nuclei of Cd11b-positive cells.

FIG. 2A shows results of evaluation by qPCR of mRNA production of cytokines, chemokines, and iNOS when treated with lipopolysaccharide (LPS). FIG. 2B shows results of quantification by ELISA of cytokines produced upon LPS stimulation. FIG. 2C shows results of qPCR analyses on the production of indicated cytokines in the presence or absence of Nrf2.

FIG. 3A shows an experimental scheme. FIG. 3B shows representative images of iPSC-derived dopaminergic neurons (DA neurons) transplanted in striatum tissues of mice. FIG. 3C shows results of quantitative analyses on transplanted cells.

FIG. 4A shows an experimental scheme. FIG. 4B shows representative images of substantia nigra of treated animals. FIG. 4C shows results of quantification of the number of TH-positive cells in substantia nigra par compacta (SNpc). FIG. 4D shows results of quantitative analyses of glial activation by qPCR on striatum tissues at day 1 from last LPS injection. FIGS. 4E and 4F show results of analyses by qPCR (FIG. 4E) and ELISA (FIG. 4F) on the levels of indicated cytokines and chemokines from striatum tissues at Day 1.

FIG. 5A shows representative images of hiPSC-derived dopaminergic neuron progenitors. FIG. 5B shows quantitative analyses of the number of hNuclei. FIG. 5C shows quantification by PCR.

DESCRIPTION OF EMBODIMENTS

Figure 1A:
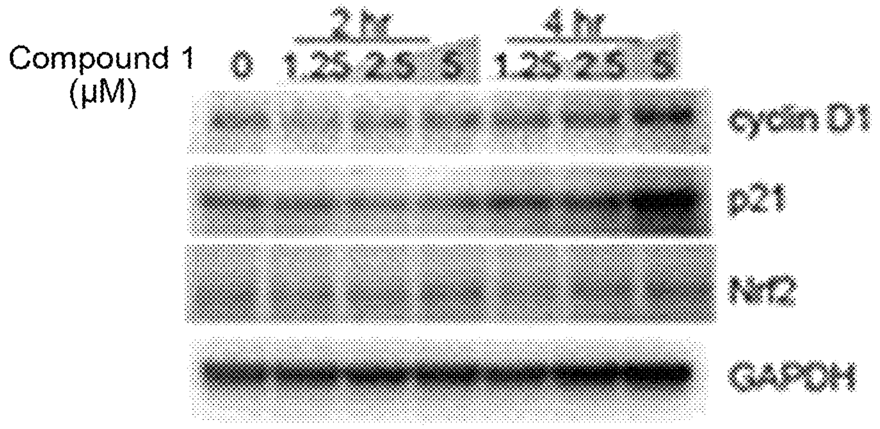
FIGS. 1A to 1C relate to the induction of p21 and Nrf2 in glial cells.

The present disclosure is based on the finding that a compound having an inhibiting ability against phosphorylation activity of DYRK1A protein can suppress neuro-inflammation.

In addition, the present disclosure is based on the finding that a compound having an inhibiting ability against phosphorylation activity of DYRK1A protein can enhance the settlement rate (survival rate, retention rate) of neuron transplanted in the brain.

In addition, the present disclosure is based on the finding that a compound having an inhibiting ability against phosphorylation activity of DYRK1A protein can promote stabilization of Nrf2 protein in glial cells and protect nerve cells from neuro-inflammation.

Regarding the mechanism in which a compound having an inhibiting ability against phosphorylation activity of DYRK1A protein exhibits an effect of suppressing neuro-inflammation, details are not clarified, but the following deduction can be made.

Microglia playing a role of supporting nerves during a normal time is activated when stress such as damage or neuro-inflammation is applied thereto, and releases proinflammatory cytokines and reactive oxygen species, thereby degenerating neurons. Here, inhibiting DYRK1A stabilizes cyclin D1 and p21, and stops Nrf2 degradation, thereby stabilizing Nrf2. This Nrf2 suppresses the expression of a gene producing proinflammatory cytokines, which suppresses excessive microglial activation. It is considered that the suppression of the activation of microglia serving as a starting point of neuro-inflammation allows the effect of the enhancement of transplantation efficacy and/or the protection of nerve cells to be exhibited.

The present disclosure, however, when interpreted, does not have to be limited to these mechanisms.

[Anti-Neuroinflammatory Drug]

The present disclosure relates to a pharmaceutical composition for suppressing neuro-inflammation, the pharmaceutical composition containing, as an active ingredient, a compound having an inhibiting ability against phosphorylation activity of DYRK1A protein, or a pharmaceutically acceptable salt of the compound (this pharmaceutical composition is hereinafter referred to as an anti-neuroinflammatory drug according to the present disclosure).

In one or a plurality of embodiments, the anti-neuroinflammatory drug according to the present disclosure is capable of suppressing neuro-inflammation by suppressing excessive microglial activation.

In one or a plurality of embodiments, the anti-neuroinflammatory drug according to the present disclosure is capable of suppressing excessive microglial activation by promoting the stabilization of Nrf2 protein in glial cells, thereby suppressing neuro-inflammation.

The "glial cell" in the present disclosure refers to non-neuron cells that support neurons (nerve cells), and in one or a plurality of embodiments, the glial cell includes microglia, astrocyte, or oligodendrocyte, and preferably the glial cell is microglia.

Nrf2 is a transcription factor that is important for homeostasis of a living body.

In the present disclosure, "stabilizing Nrf2 protein" refers to suppressing the Nrf2 degradation, thereby increasing the amount of Nrf2 protein in cells, in one or a plurality of embodiments. The stabilization of Nrf2 can be confirmed with reference to Examples, in one or a plurality of embodiments.

In one or a plurality of embodiments, the anti-neuroinflammatory drug according to the present disclosure may be formed in a dosage form suitable for an administration form by using the known formulation technology. The pharmaceutical composition can be administered, for example, orally in such a dosage form as tablets, capsules, granules, powder, pills, troches, syrups, and liquid formulations, though the dosage form is not limited to these. Alternatively, the pharmaceutical composition can be administered parenterally in such a dosage form as injections, liquid formulations, aerosols, suppositories, patches, cataplasm, lotions, liniments, ointments, and eye drops. These formulations can be produced by a known method using additives such as excipients, lubricants, binders, disintegrators, stabilizers, corrigents, and diluents, though the additives are not limited to these. In one or a plurality of embodiments, the pharmaceutical composition of the present disclosure may further contain a pharmaceutically acceptable carrier, preservative, surfactant, pH adjuster, diluent, or additive described above, or another pharmaceutically acceptable component.

The excipient is, for example (though not limited to), a starch such as starch, potato starch, or corn starch; lactose; crystalline cellulose; or calcium hydrogen phosphate. The lubricant is, for example (though not limited to), ethyl cellulose; hydroxypropyl cellulose; hydroxypropyl methylcellulose; shellac; talc; carnauba wax; or paraffin. Examples of the binder include (though not limited to) the following: polyvinyl pyrrolidone; macrogol; and the same compounds as those given as examples of the excipient. Examples of the disintegrator include (though not limited to) the following: compounds similar to those given as examples of the excipient; and chemically modified starches and celluloses such as croscarmellose sodium, sodium carboxymethyl starch, and cross-linked polyvinyl pyrrolidone. Examples of the stabilizer include (though not limited to) the following: paraoxybenzoic acid esters such as methylparaben and propylparaben; alcohols such as chlorobutanol, benzyl alcohol, and phenylethyl alcohol; benzalkonium chloride; phenols such as phenol and cresol; thimerosal; dehydroacetic acid; and sorbic acid. The corrigent is, for example (though not limited to), a commonly used sweetener, an acidulant, or a flavor.

The preparation of a liquid formulation may use ethanol, phenol, chlorocresol, purified water, or distilled water as a solvent, though the solvent is not limited to these, and may also use a surface-active agent or an emulsifying agent as required. The surface-active agent or the emulsifying agent is, for example (though not limited to), polysorbate 80, polyoxyl 40 stearate, or lauromacrogol.

The anti-neuroinflammatory drug according to the present disclosure may be administered to, for example, a subject who affects by a disease accompanied by neuro-inflammation. In one or a plurality of embodiments, the disease accompanied by neuro-inflammation is frontotemporal lobar degeneration, amyotrophic lateral sclerosis, or multiple sclerosis.

The subject is, for example, a human, or an animal other than a human. In one or a plurality of embodiments, examples of the animal include the mammals such as mouse, rat, guinea pig, hamster, rabbit, cat, dog, sheep, pig, cow, horse, goat, and monkey.

The dose amount of the anti-neuroinflammatory drug according to the present disclosure may differ depending on symptoms, ages, administration methods, etc.

Regarding how to use the anti-composition, the anti-neuroinflammatory drug can be intermittently or continuously administered, for example, orally, percutaneously, submucosally, subcutaneously, intramuscularly, intravascularly, intracerebrally, or intraperitoneally so that the concentration of the compound as an active ingredient in the body is in the range of 100 nM to 1 mM, though the method for using the composition is not limited to these.

In a non-limiting embodiment, for oral administration, the anti-neuroinfiammatory drug may be administered to a subject (e.g., an adult human if the subject is a human) based on the symptom, in a daily dosage of from 0.01 mg (preferably 0.1 mg) as a lower limit to 2000 mg (preferably 500 mg and more preferably 100 mg) as an upper limit, which is expressed in terms of the compound as an active ingredient, at once or in batches. In a non-limiting embodiment, for intravenous administration, the anti-neuroinflammatory drug may be administered to a subject (e.g., an adult human if the subject is a human) based on the symptom, in a daily dosage of from 0.001 mg (preferably 0.01 mg) as a lower limit to 500 mg (preferably 50 mg) as an upper limit, at once or in batches.

In another aspect, the present disclosure therefore relates to a method for suppressing neuro-inflammation, the method including administering, to a subject, an effective amount of the anti-neuroinflammatory drug according to the present disclosure.

In addition, in another aspect, the present disclosure relates to a method for suppressing excessive microglial activation and suppressing neuro-inflammation, the method including administering, to a subject, an effective amount of the anti-neuroinflammatory drug according to the present disclosure.

In addition, in another aspect, the present disclosure relates to a method for suppressing excessive microglial activation by promoting the stabilization of Nrf2 protein, and suppressing neuro-inflammation, the method including administering, to a subject, an effective amount of the anti-neuroinflammatory drug according to the present disclosure.

In addition, in another aspect, the present disclosure relates to a method for ameliorating, suppressing progression of, and/or treating a disease accompanied by neuro-inflammation, the method including administering, to a subject, an effective amount of the anti-neuroinflammatory drug according to the present disclosure.

[Transplantation Adjuvant]

In one aspect, the present disclosure relates to a pharmaceutical composition for assisting the transplantation of neuron precursor cells, pluripotent stem cells, and/or neurons, the pharmaceutical composition containing, as an active ingredient, a compound having an inhibiting ability against phosphorylation activity of DYRK1A protein or a pharmaceutically acceptable salt of the compound (this pharmaceutical composition is hereinafter also referred to as a transplantation adjuvant according to the present disclosure).

In the present disclosure, in one or a plurality of embodiments, the transplantation of cells refers to transplanting cells to a specific site of a transplantation subject (recipient), causing the cells to be engrafted (settled) in the site where the cells are transplanted and/or a surrounding site, and/or causing the cells to differentiate appropriately according to surrounding environments.

In one or a plurality of embodiments, the specific site where the cells are transplanted is the nervous system, the central nervous system (for example, the brain and the spinal cord), the peripheral nerve system, or tissues of these.

In the present disclosure, in one or a plurality of embodiments, "assisting transplantation" refers to improving the post-transplantation survival rate, settlement rate, and/or retention rate of transplanted cells. The improvement of the survival rate, settlement rate, and/or retention rate of cells can be confirmed with reference to Examples, in one or a plurality of embodiments.

In the present disclosure, in one or a plurality of embodiments, the "transplantation of neuron precursor cells, pluripotent stem cells, and/or neurons" may be the transplantation in such a form that these cells per se are transplanted, the transplantation in such a form that other cells are also transplanted together, or the transplantation in such a form that neuron precursor cells, stem cells, and/or neurons are included in a part of an organ, a tissue, or an aggregate.

In the present disclosure, the "neuron precursor cell" refers to a cell that can differentiate into a nerve cell, and the differentiation stage is not limited in particular.

In one or a plurality of embodiments, the neuron precursor cell used in the present disclosure may be a neural stem cell. In one or a plurality of embodiments, the neuron precursor cell used in the present disclosure may be a cell isolated from a brain tissue of a mammal such as a human. In one or a plurality of embodiments, the neuron precursor cell used in the present disclosure may be a cell obtained by differentiation induction of a pluripotent stem cell such as an embryonic stem cell (ES cell) and a human induced pluripotent stem cell (iPS cell) (also referred to as an ES cell-derived cell, and iPS cell-derived cell, respectively).

In one or a plurality of embodiments, the pluripotent stem cell used in the present disclosure is a pluripotent stem cell, or a neural stem cell, which can differentiate into a nerve cell. In one or a plurality of embodiments, the pluripotent stem cell is an ES cell, and an iPS cell, a cloned embryo-derived embryonic stem (ntES) cell obtained by nuclear transplantation, a germline stem cell (GS cell), an embryonic germline cell (EG cell), a culture fibroblast, or a bone marrow stem cell-derived pluripotent stem cell (Muse cell).

In one or a plurality of embodiments, the neuron (nerve cell) is, though not particularly limited to, a neuron differentiation-induced from a neuron precursor cell.

In one or a plurality of embodiments, the neuron precursor cell and neuron to be transplanted are a dopaminergic neuron precursor cell differentiation-induced from a pluripotent stem cell and a dopaminergic neuron differentiation-induced from a pluripotent stem cell.

The transplantation adjuvant according to the present disclosure can be used so as to be administered to a transplantation subject (recipient) before the transplantation to the recipient, simultaneously with the transplantation, or after the transplantation.

Alternatively, the transplantation adjuvant may be added to cells to be transplanted, before the transplantation.

The recipient is, for example, a human, or a mammal other than a human. In one or a plurality of embodiments, examples of the animal include the mammals such as mouse, rat, guinea pig, hamster, rabbit, cat, dog, sheep, pig, cow, horse, goat, and monkey.

The cells to be transplanted can be cells of the human or the animal other than a human.

The species of the recipient and the species of the cells to be transplanted may be the same, or may be different.

The dose amount of the transplantation adjuvant according to the present disclosure may differ depending on the purpose of administration, the administering method, and the states (sex, age, body weight, symptom, etc.) of a subject of administration. When it is administered to a human, in one or a plurality of embodiments, the transplantation adjuvant may be used so that an active ingredient is administered in a daily dosage of 10 to 1200 mg, or 100 to 1200 mg. Alternatively, these may be identical to those for the above-described anti-neuroinflammatory drug according to the present disclosure.

Regarding the route of administration of the transplantation adjuvant according to the present disclosure, the transplantation adjuvant can be brought into direct contact to a part or cells subjected to the transplantation, or may be administered orally, transdermally, submucosally, subcutaneously, intramuscularly, intravascularly, intracerebrally, or intraperitoneally. Regarding the commonly used administration form of the transplantation adjuvant, it can be administered, for example, in tablets, capsules, granules, fine granules, powder, sublingual tablets, syrups, and suspensions. The transplantation adjuvant in a liquid formulation form may be parenterally administered as an injection agent. The above-described administration dosage form can be produced by formulating the active ingredient according to the present disclosure in an acceptable normal carrier, excipient, binder, stabilizer, etc. When the transplantation adjuvant according to the present disclosure is used as an injection agent, an acceptable buffer, solubilizer, isotonic agent, etc. can be added thereto.

With use of the transplantation adjuvant according to the present disclosure, in one or a plurality of embodiments, the post-transplantation survival rate, settlement rate, and/or retention rate of neurons in a subject can be improved.

The transplantation adjuvant according to the present disclosure, in one or a plurality of embodiments, therefore can be used in transplantation of an organ, a tissue, or cells for regenerative medicine.

In addition, the transplantation adjuvant according to the present disclosure, in one or a plurality of embodiments, can be used in transplantation in a surgery (treatment) of a neurologic disease, for example, a neurodegenerative disease exhibiting progressive neurologic deficits such as cerebral infarction, infarction of spinal cord, cerebral hemorrhage, hematomyelia, facial paralysis, limb paralysis, dementia with lewy bodies, Down syndrome, depression, neurodegenerative disease, Alzheimer's disease, Parkinson's disease, Huntington's disease.

In another aspect, therefore, the present disclosure relates to a method for increasing a survival rate of transplanted neuron precursor cells, pluripotent stem cells, and/or neurons, the method including administering, to a recipient, an effective amount of the transplantation adjuvant according to the present disclosure before, simultaneously with, or after transplantation of the neuron precursor cells, pluripotent stem cells, and/or neurons.

In addition, in another aspect, therefore, the present disclosure relates to a method for transplanting neuron precursor cells, pluripotent stem cells, and/or neurons, the method including administering, to a recipient, an effective amount of the transplantation adjuvant according to the present disclosure before, simultaneously with, or after the transplantation.

[Nrf2 Stabilizer]

In one aspect, the present disclosure relates to a pharmaceutical composition for promoting the stabilization of Nrf2 protein in glial cells, the pharmaceutical composition containing, as an active ingredient, a compound having an inhibiting ability against phosphorylation activity of DYRK1A protein, or a pharmaceutically acceptable salt of the compound (this pharmaceutical composition is hereinafter also referred to as an Nrf2 stabilizer according to the present disclosure).

In one or a plurality of embodiments, the Nrf2 stabilizer according to the present disclosure is capable of promoting the stabilization of Nrf2 protein in glial cells. In one or a plurality of embodiments, the Nrf2 stabilizer according to the present disclosure is capable of promoting the stabilization of Nrf2 protein in glial cells, thereby suppressing excessive activation of glial cells. As the activation of microglia serves as a starting point of neuro-inflammation, the Nrf2 stabilizer according to the present disclosure, in one or a plurality of embodiments, is capable of suppressing the activation of glial cells and suppressing neuro-inflammation.

The administration form, dosage form, dose amount, and the like of the Nrf2 stabilizer according to the present disclosure may be set identical to those of the anti-neuroinflammatory drug according to the present disclosure.

The Nrf2 stabilizer according to the present disclosure may be administered to, for example, a subject who affects by a disease accompanied by neuro-inflammation. In one or a plurality of embodiments, the disease accompanied by neuro-inflammation is frontotemporal lobar degeneration, amyotrophic lateral sclerosis, or multiple sclerosis.

The subject is, for example, a human, or an animal other than a human.

In another aspect, therefore, the present disclosure relates to a method for promoting the stabilization of Nrf2 protein in glial cells, the method including administering, to a subject, an effective amount of the Nrf2 stabilizer according to the present disclosure.

In addition, in another aspect, the present disclosure relates to a method for promoting the stabilization of Nrf2 protein in glial cells and suppressing neuro-inflammation, the method including administering, to a subject, an effective amount of the Nrf2 stabilizer according to the present disclosure.

In addition, in another aspect, the present disclosure relates to a method for ameliorating, suppressing progression of, and/or treating a disease accompanied by neuro-inflammation, the method including administering, to a subject, an effective amount of the Nrf2 stabilizer according to the present disclosure.

[Nerve Cell Protective Agent]

In one aspect, the present disclosure relates to a pharmaceutical composition for protecting nerve cells from neuro-inflammation, the pharmaceutical composition containing, as an active ingredient, a compound having an inhibiting ability against phosphorylation activity of DYRK1A protein, or a pharmaceutically acceptable salt of the compound (this pharmaceutical composition is hereinafter also referred to as a nerve cell protective agent according to the present disclosure).

In one or a plurality of embodiments, the nerve cell protective agent according to the present disclosure is capable of suppressing excessive activation of glial cells by promoting the stabilization of Nrf2 protein in glial cells. As the activation of microglia serves as a starting point of neuro-inflammation, neuro-inflammation can be suppressed by suppressing the activation of glial cells, whereby the protection of nerve cells can be achieved.

The administration form, dosage form, dose amount, and the like of the nerve cell protective agent according to the present disclosure may be set identical to those of the anti-neuroinflammatory drug according to the present disclosure.

The nerve cell protective agent according to the present disclosure may be administered to, for example, a subject who affects by a disease accompanied by neuro-inflammation. In one or a plurality of embodiments, the disease accompanied by neuro-inflammation is frontotemporal lobar degeneration, amyotrophic lateral sclerosis, or multiple sclerosis.

The subject is, for example, a human, or an animal other than a human.

In another aspect, the present disclosure therefore relates to a method for protecting nerve cells from neuro-inflammation, the method including administering, to a subject, an effective amount of the nerve cell protective agent according to the present disclosure.

In addition, in another aspect, the present disclosure relates to a method for protecting nerve cells by suppressing neuro-inflammation, the method including administering, to a subject, an effective amount of the nerve cell protective agent according to the present disclosure.

In addition, in another aspect, the present disclosure relates to a method for protecting nerve cells by suppressing the activation of glial cells thereby suppressing neuro-inflammation, the method including administering, to a subject, an effective amount of the nerve cell protective agent according to the present disclosure.

In addition, in another aspect, the present disclosure relates to a method for ameliorating, suppressing progression of, and/or treating a disease accompanied by neuro-inflammation, the method including administering, to a subject, an effective amount of the nerve cell protective agent according to the present disclosure.

[Active Ingredient]

The active ingredient of the pharmaceutical composition (anti-neuroinflammatory drug, transplantation adjuvant, Nrf2 stabilizer, and nerve cell protective agent) according to the present disclosure (hereinafter also referred to as the active ingredient according to the present disclosure) is a compound having an inhibiting ability against phosphorylation activity of DYRK1A protein, or a pharmaceutically acceptable salt of the compound.

In one or a plurality of embodiments, as the compound having an inhibiting ability against phosphorylation activity of DYRK1A protein, those disclosed in WO2018/043674 and WO2015/107945 can be used. The contents of these documents are incorporated as constituting a part of the present disclosure.

DYRK1A phosphorylates cyclin D1, thereby promoting the decomposition of cyclin D1 and p21.

In one or a plurality of embodiments, the compound having an inhibiting ability against phosphorylation activity of DYRK1A protein in the present disclosure is at least one selected from the group consisting of compounds expressed by Formulae (I) to (III) shown below:

(I)

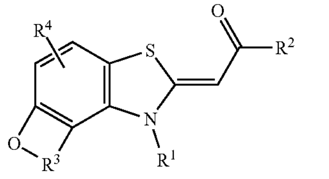

(II)

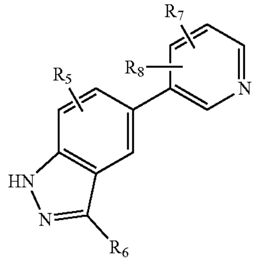

(III)

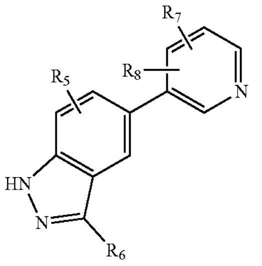

where, in Formula (I), $R^1$ and $R^2$ independently represent a hydrogen atom or a hydrocarbon chain having 1 to 6 carbon atoms, $R^3$ represents $—CH_2—CH_2—$ or $—CH═CH—$, and $R^4$ represents a hydrogen atom, a halogen atom, or an alkyl group having 1 to 6 carbon atoms, and in Formulae (II) and (III), $R^5$, $R^6$, $R^7$ and $R^8$ independently represent a hydrogen atom, a halogen atom, a carboxyl group, an amino group, a hydroxyl group, an alkyl group having 1 to 4 carbon atoms, or a halogen-atom-substituted alkyl group having 1 to 4 carbon atoms.

In Formula (I), $R^1$ represents an alkyl group having 1 to 6 carbon atoms in one or a plurality of embodiments, and represents a methyl group, an ethyl group, or a propyl group in another one or more embodiments. In Formula (I), $R^2$ represents an alkyl group having 1 to 6 carbon atoms in one or a plurality of embodiments, and represents a methyl group in another one or more embodiments. In Formula (I), $R^4$ represents a hydrogen atom in one or a plurality of embodiments.

In one or a plurality of embodiments, the compound expressed by Formula (I) is a compound expressed by either one of the following:

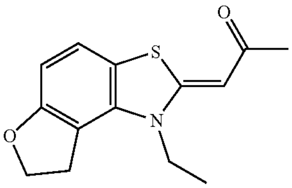

,

-continued

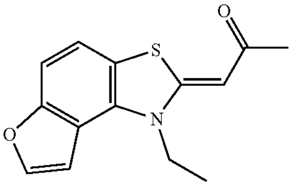

,

In Formulae (II) and (III), $R^5$, $R^6$, $R^7$, and $R^8$ represent hydrogen atoms in one or a plurality of embodiments.

In one or a plurality of embodiments, the compounds expressed by Formulae (II) and (III) are compounds expressed by:

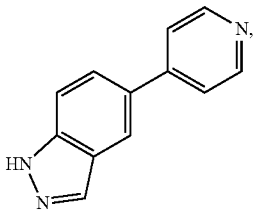

,

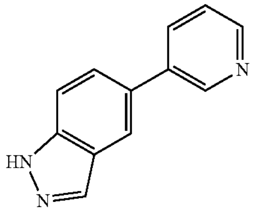

In the present disclosure, the "pharmaceutically acceptable salt" contains a pharmacologically and/or pharmaceutically acceptable salt. It is, for example, an inorganic acid salt, an organic acid salt, an inorganic base salt, an organic base salt, an acidic amino acid salt, or a basic amino acid salt.

Preferable examples of the inorganic acid salt include a hydrochloride, a hydrobromate, a sulfate, a nitrate, and a phosphate. Preferable examples of the organic acid salt include an acetate, a succinate, a fumarate, a maleate, a tartrate, a citrate, a lactate, a stearate, a benzoate, a methanesulfonate, and a p-toluenesulfonate.

Preferable examples of the inorganic base salt include a salt of an alkali metal such as a sodium salt or a potassium salt, an alkali earth metal salt such as a magnesium salt or a calcium salt, an aluminum salt, and an ammonium salt. Preferable examples of the organic base salt include a diethylamine salt, a diethanolamine salt, a meglumine salt, and an N,N'-dibenzylethylenediamine salt.

Preferable examples of the acidic amino acid salt include an aspartate, and a glutamate. Preferable examples of the basic amino acid salt include an arginine salt, a lysine salt, and an ornithine salt.

In the present disclosure, the "salt of a compound" may encompass a hydrate that can be formed when a compound, left in the atmosphere, absorbs moisture. Further, in the present disclosure, the "salt of a compound" may also encompass a solvate that can be formed when a compound absorbs a solvent of a certain kind.

In one or a plurality of embodiments, the alkyl group in the present disclosure is a straight or branched chain or cyclic alkyl group. In one or a plurality of embodiments, the "alkyl group having 1 to 4 carbon atoms" in the present disclosure is a straight or branched chain alkyl group having 1, 2, 3, or 4 carbon atoms, or a cyclic alkyl group having 3 or 4 carbon atoms. In one or a plurality of embodiments, the straight or branched chain alkyl group having 1, 2, 3, or 4 carbon atoms is a methyl group, an ethyl group, a propyl group, an isopropyl group, an n-butyl group, an isobutyl group, a sec-butyl group, or a tert-butyl group. In one or a plurality of embodiments, the cyclic alkyl group having 3 or 4 carbon atoms is a cyclopropyl group, or a cyclobutyl group.

The "hydrocarbon chain having 1 to 6 carbon atoms" in the present disclosure refers to a monovalent group derived from an aliphatic hydrocarbon having 1, 2, 3, 4, 5, or 6 carbon atoms by removing one arbitrary hydrogen atom therefrom. In one or a plurality of embodiments, the hydrocarbon chain may have a straight chain structure or a branched chain structure, and examples of the same include an alkyl group, an alkenyl group, a phenyl group, and a cycloalkyl group. In one or a plurality of embodiments, the "alkyl group having 1 to 6 carbon atoms" in the present disclosure is a methyl group, an ethyl group, a 1-propyl group, a 2-propyl group, a 2-methyl-1-propyl group, a 2-methyl-2-propyl group, a 1-butyl group, a 2-butyl group, a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, a 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group, or a 2,3-dimethyl-2-butyl group.

In one or a plurality of embodiments, the halogen atom in the present disclosure is a fluorine atom, a chlorine atom, a bromine atom, or an iodine atom.

The present disclosure may relate to one or a plurality of embodiments described below:

[1] A pharmaceutical composition for suppressing neuro-inflammation, the pharmaceutical composition containing, as an active ingredient, a compound having an inhibiting ability against phosphorylation activity of DYRK1A protein, or a pharmaceutically acceptable salt of the compound.

[2] The pharmaceutical composition according to [1], for assisting transplantation of neuron precursor cells, pluripotent stem cells, and/or neurons.

[3] The pharmaceutical composition according to [1], for promoting the stabilization of Nrf2 protein in glial cells.

[4] The pharmaceutical composition according to [1], for protecting nerve cells from neuro-inflammation.

[5] The pharmaceutical composition according to [1], for ameliorating, suppressing progression of, and/or treating a disease accompanied by neuro-inflammation selected from the group consisting of frontotemporal lobar degeneration, amyotrophic lateral sclerosis, and multiple sclerosis.

[6] The pharmaceutical composition according to any one of [1] to [5], wherein the compound having an inhibiting ability against phosphorylation activity of DYRK1A protein is at least one selected from the group consisting of compounds expressed by Formulae (I) to (III) shown below:

(I)

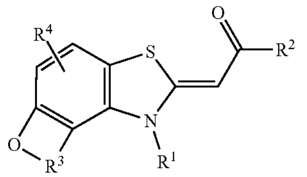

-continued (II)

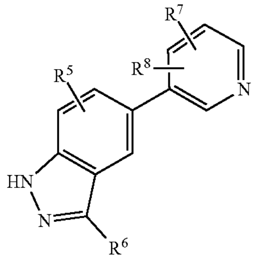

(III)

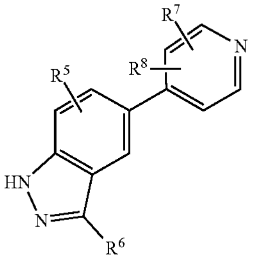

where, in Formula (I), $R^1$ and $R^2$ independently represent a hydrogen atom or a hydrocarbon chain having 1 to 6 carbon atoms, $R^3$ represents $—CH_2—CH_2—$ or $—CH{=}CH—$, and $R^4$ represents a hydrogen atom, a halogen atom, or an alkyl group having 1 to 6 carbon atoms, and in Formulae (II) and (III), $R^5$, $R^6$, $R^7$ and $R^8$ independently represent a hydrogen atom, a halogen atom, a carboxyl group, an amino group, a hydroxyl group, an alkyl group having 1 to 4 carbon atoms, or a halogen-atom-substituted alkyl group having 1 to 4 carbon atoms.

[7] A method for suppressing neuro-inflammation, the method including administering, to a subject, an effective amount of the pharmaceutical composition according to any one of [1] to [6].

[8] A method for increasing a survival rate, a settlement rate, and/or a retention rate of transplanted neuron precursor cells, pluripotent stem cells, and/or neurons, the method including administering, to a recipient, an effective amount of the pharmaceutical composition according to any one of [1] to [6] before, simultaneously with, or after transplantation of neuron precursor cells, pluripotent stem cells, and/or neurons.

[9] A method for promoting stabilization of Nrf2 protein in glial cells, the method including administering, to a subject, an effective amount of the pharmaceutical composition according to any one of [1] to [6].

[10] A method for protecting nerve cells from neuro-inflammation, the method including administering, to a subject, an effective amount of the pharmaceutical composition according to any one of [1] to [6].

[11] A method for ameliorating, suppressing progression of, and/or treating a disease accompanied by neuro-inflammation selected from the group consisting of frontotemporal lobar degeneration, amyotrophic lateral sclerosis, and multiple sclerosis, the method including administering, to a subject, an effective amount of the pharmaceutical composition according to any one of [1] to [6].

EXAMPLE

Hereinafter, although the following description describes the present disclosure in more detail by way of examples, these are illustrative, and the present disclosure is not limited to these examples. Note that all of the documents cited in the present disclosure are incorporated as a part of the present disclosure.

Compound 1

The following compound 1 was synthesized by the method disclosed in WO2018/043674. The compound 1 had an $IC_{50}$ of 76.95 nM in in vitro kinase activity against DYRK1A.

Compound 1

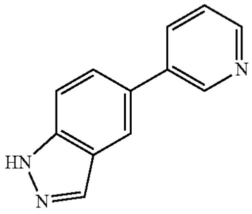

Compound 2

The following compound 2 was synthesized by the method disclosed in WO2015/083750. The compound 2 had an $IC_{50}$ of 32.95 nM in in vitro kinase activity against DYRK1A.

Compound 2

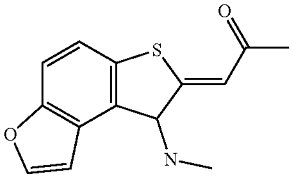 [SMILES: CCN1/C(=C/C(C)=O)Sc2ccc3occc3c21]

Statistics

Statistics results obtained from three or more experiments are expressed as the mean±SEM. Statistically significant differences were determined using a two-tailed, unpaired Student's test or one-way analysis of variance (ANOVA) followed by a Tukey-Kramer comparison test. A P value of less than 0.05 was considered to be significant and marked with a single asterisk (*), and a P value less than 0.01 was marked with a double asterisk (**).

Image Analysis

Cells were plated in 96-well purecoat amine coated plates and treated as desired for each specific experiment. After immunolabeling was complete, automated image acquisition (with twenty-fold magnification of objective lens, 2×2 CCD binning, twenty-five fields per well) and analysis was performed using Opera Phenix (manufactured by PerkinElmer Co., Ltd.) equipped with Harmony software. Image acquisition was performed using a fluorescence microscope (BZ-9000, manufactured by Keyence corporation) or a confocal microscope (SP-8, manufactured by Leica) as well.

Animal Model

C57black/6J mice, 8 to 9-week old, were intraperitoneally injected with LPS (O55:B5) (manufactured by Sigma, L2880) at 1 mg/kg once daily for four days. hiPSC-derived dopaminergic (DA) progenitors were transplanted in striatum of 4-week-old SCID mice. Drug treatment was performed one hour before LPS-injection or iPSC transplantation.

Reagent

Lipopolysaccharide (LPS) was obtained from Sigma-Aldrich. Small molecule compounds were dissolved in dimethyl sulfoxide (DMSO, manufactured by Nacalai Tesque) to produce a stock solution of 50 mM for assays in vitro. siRNAs were purchased from Ambion or Dharmacon. Rabbit polyclonal anti-Nrf2 (MBL) for Western blotting, rabbit polyclonal anti-Nrf2 (abcam) for immunocytochemistry, mouse monoclonal anti-p21 (abcam), rabbit polyclonal anti-cyclin D1 (Cell Signaling), rat anti-CD11b (abcam), chicken polyclonal anti-TH (abcam), rabbit polyclonal anti-Iba1 (Wako), goat polyclonal anti-GFAP (Millipore), rat anti-Nurr1 (donated by the KAN laboratory), mouse monoclonal anti-hNuclei (abcam), and rabbit polyclonal HRP-conjugated anti-GAPDH (MBL) were used.

Cell Culture

Microglial cell line BV-2 was maintained in high glucose Dulbecco's modified Eagle's medium (DMEM) (Nacalai Tesque) supplemented with 10% fetal bovine serum (Nichirei Biosciences), 100 U/mL penicillin, and 100 μg/mL streptomycine. Primary hippocampal and cortical neuronal cultures were prepared from embryonic day 18 mice and maintained in Neurobasal medium (Life Technologies) supplemented with 2% B27 supplement, 100 U/mL, penicillin, 100 μg/mL streptomycin, and 0.5 mM L-glutamine. Dopaminergic neuronal cultures were prepared from ventral midbrain of embryonic day 13 mice and maintained in Neurobasal medium (Life Technologies) supplemented with 10% fetal bovine serum, 2% B27 supplement, 10 ng/mL GDNF, 100 U/mL penicillin, and 100 μg/mL streptomycin. For depletion of glial cells, 5 μM cytosine β-D-arabinofuranoside, 10 μM 5-fluorouracil, and 10 μM uridine (all from Sigma-Aldrich) were added at 2-day culture. Mixed glial cultures were obtained from new born murine pups (P1 to P4) and maintained in T75 or T175 flask. Media were changed every 3-4 days until the cells get confluent. Microglia were obtained either by shaking vigorously or Cd11b-positive selection (Invitrogen). For co-culture experiments, murine glial cell cultures were prepared from MGE (Medial Ganglionic Eminence) of embryonic day 13 and cultured in PLL-coated dish. Cultures were passaged twice with trypsin, and used for co-cultured assay with iPSC-derived neurons. 1039A1 iPS cells were established and maintained as described previously (Nakagawa et al., Sci Rep 4, 3594, 2014). Induction of dopaminergic precursor cells was performed as described previously (Doi et al., Stem Cell Reports 2, 337-350, 2014, Kikuchi et al., Nature 548, 592-596, 2017). Briefly, hiPS cells 1039A1 were plated on Laminin511, and differentiated in GMEM medium containing 8% KSR, Y27632 (Wako), A-83-01 (Wako), LDN193178 (STEMGENT). Purmorphamine (Wako), FGF8 (Wako, from day 1 to day 7), and CHIR99021 (Wako, from day 3 to day 12) were added. After cell sorting of Corin+ cells, cells were replated onto low attachment 96-well plates for neurosphere cultures and maintained in neurobasal medium with B27 supplement, 2 mM L-glutamine (Invitrogen), 10 ng/mL GDNF, 200 μM ascorbic acid, 20 ng/mL BDNF (all from Wako), and 400 μM dbcAMP (Sigma-Aldrich) for further 2 weeks. To avoid apoptosis, 30 μM of Y27632 (Wako) was added at the initial plating.

Immunocytochemistry

Cells were fixed with 4% paraformaldehyde for 10 minutes, followed by permealization with 0.2% TritonX-100 for 10 minutes. After washing in PBS, cells were blocked in 5% normal donkey serum (Jackson ImmunoResearch Laboratories)/1% BSA (SIGMA A7906)/PBS and then labeled with the primary antibodies. After washing with PBS, primary antibodies were labeled with the corresponding fluorescence-conjugated secondary antibodies. Hoechst 33342 was used to detect nuclei.

RNA Extraction and Quantitative RT-PCR

Total RNA was extracted with RNeasy kit (Qiagen) followed by cDNA synthesis using iScript (Bio-Rad). Quantitative PCRs were carried out with SYBR green ExTaq (TaKaRa). Primers for genes were designed by using PrimerBank (Wang et al., 2012).

Immunoblotting

Total protein was extracted from cell culture samples using RIPA buffer (Wako) containing protease inhibitor cocktail (Nacalai Tesque) and phosphatase inhibitor cocktail (Nacalai Tesque). After 15 minutes of centrifugation at 15,000 rpm at 4° C., supernatants were collected and protein concentrations were measured using a Pierce 660 nm Protein Assay Kit (Thermo Scientific). Proteins were then separated with 5 to 20% gradient SDS/PAGE gel (ATTO) and transferred onto polyvinylidene fluoride membranes (Millipore) by electroblotting. Membranes were blocked with Blocking One (Nacalai Tesque) and then probed with indicated antibodies. Detection was performed using Immunostar chemiluminescence (Wako) and a ChemiDoc imaging system (Bio-Rad).

In Vitro Enzyme Activity Assay

The in vitro kinase activity assay was performed as described previously (Ogawa et al., Nat Commun 1, 86, 2010).

Drug Treatment Studies

The compound 1 was initially dissolved in DMSO at a concentration of 100 mg/mL and diluted to desired concentration with 10% Tween 80 (polysorbate 80 (HX2), manufactured by HOF Corporation) in physiological saline solution, and subcutaneously delivered in a volume of 0.05 mL/kg. The compound 2 was suspended in 0.5% carboxymethylcellulose (Nacalai Tesque) and orally administered in a volume of 0.1 mL/kg at desired concentration. Drug-treated animals were anesthetized with isofluorane for blood sampling and subsequently perfused with physiological saline solution. Brain homogenates were prepared using the Beads Crusher μT-12 system (TAITEC) in five-volume of physiological saline solution. Concentration of target compounds or dopamine in serum and brain homogenates were analyzed by LC/MS using an Agilent 6420 Q-TOF mass spectrometer with an Agilent 1290 Nano-flow HPLC system (Agilent Technologies). For measurement of dopamine, 50 mg/mL ascorbic acid was added to avoid oxidization.

Immunohistochemistry

Adult mouse brains were perfused with PBS then fixed in 4% paraformaldehyde, and 40-μm sections were cut with a vibratome (Leica) or 20-μm sections with a cryostat (Leica) after equilibrating in 30% sucrose/PBS. After antigen retrieval using HistoOne (Nacalai Tesque), tissues were stained with indicated antibodies.

Experiment Example 1: Induction of p21 and Nrf2

The compounds 1 and 2 were confirmed to induce p21 and Nrf2 in glial cells.

FIG. 1A shows results of Western blotting analyses on microglial cells BV-2 treated with the compound 1. The BV-2 cells were treated with the compound 1 at indicated concentrations and for indicated periods. Samples after the treatment were subjected to Western blotting analysis using indicated antibodies. As shown in FIG. 1A, cyclin D1, p21, and Nrf2 were up-regulated by the compound 1 time-dependently and dose-dependently in the BV-2 cells.

Figure 1B:
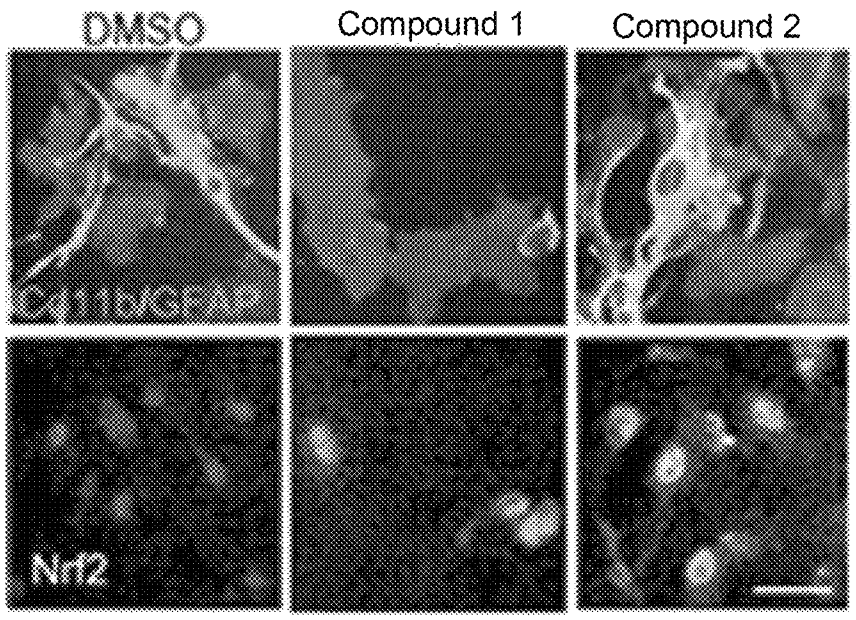

FIG. 1B shows representative images of glial cells treated with the compounds 1 and 2. Cells were visualized with anti-Nrf2 (pseudo-color), Cd11b (magenta, microglia), and GFAP (green, astrocyte) antibodies. Scale bar=25 μm.

Figure 1C:
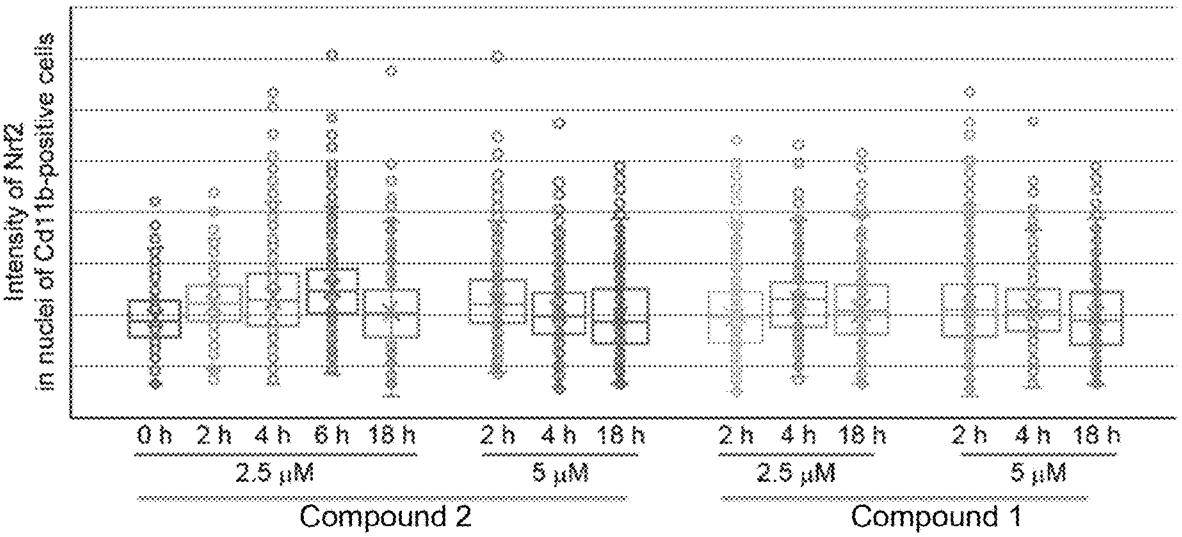

FIG. 1C shows exemplary quantification of signal intensities of Nrf2 in nuclei of Cd11b-positive cells. Glial cells were treated with the compounds 1 and 2 for indicated periods and at indicated concentrations.

It is confirmed from FIGS. 1B and 1C that the expression of Nrf2 in Cd11b-positive microglial cells is induced by the compound 1 or 2.

In addition, Nrf2 expression did not increase in p21 siRNA-treated cells even if the cells were treated with the compound 1 or 2, but Nrf2 expression increased in control siRNA-treated cells in a case where the cells were treated with the compound 1 or 2 (data not shown).

It can be considered from these that the treatment with the compound 1 or 2 mediates the induction of Nrf2 by stabilizing the cyclin D1/p21 complex.

Experiment Example 2: Compounds 1 and 2 Suppress Neuro-Inflammation Through Stabilization of Nrf2

Studies were made on whether the compounds 1 and 2 would suppress cytokine production of microglia.

Figure 2A:
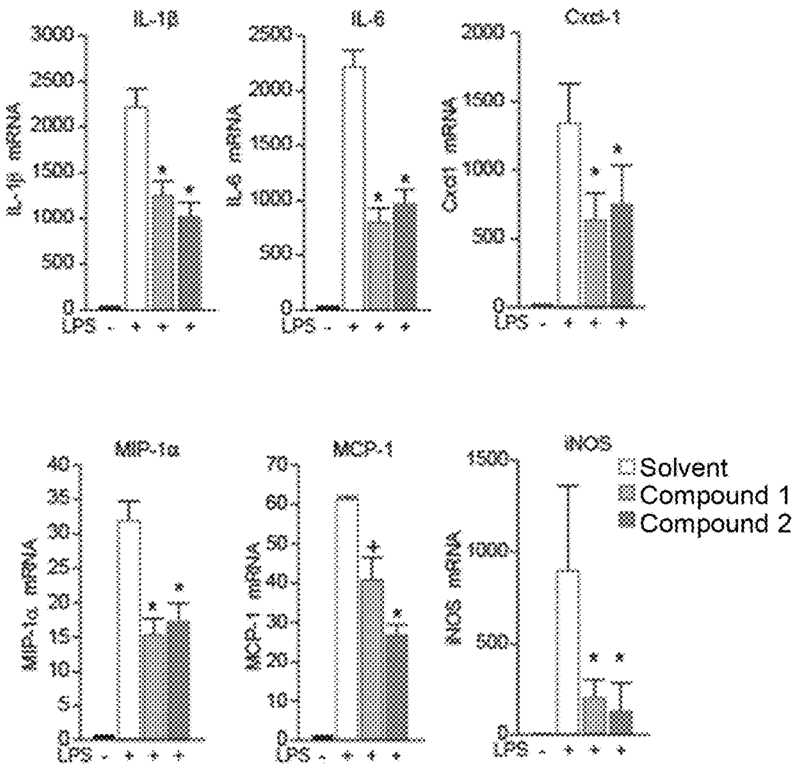
FIGS. 2A to 2C relate to the suppression of neuro-inflammation (cytokine production of microglia).

FIG. 2A shows results of evaluation by qPCR of mRNA production of cytokines, chemokines, and iNOS when treated with LPS. $^*P<0.05$.

Figure 2B:
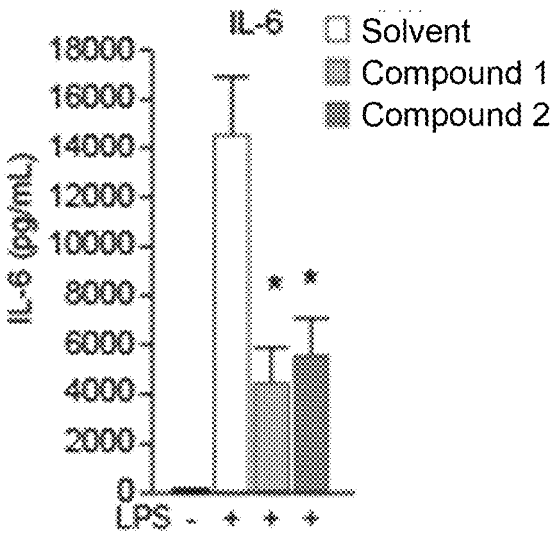

FIG. 2B shows results of quantification by ELISA of cytokines produced upon LPS stimulation. $^*P<0.05$.

As indicated by these, the LPS stimulation dramatically induces the expression of a proinflammatory cytokine gene, but these up-regulations were suppressed effectively by the treatment with the compound 1 or 2. In addition, the induction of expression of several chemokines and iNOS mRNA were also suppressed (FIG. 2A).

Figure 2C:
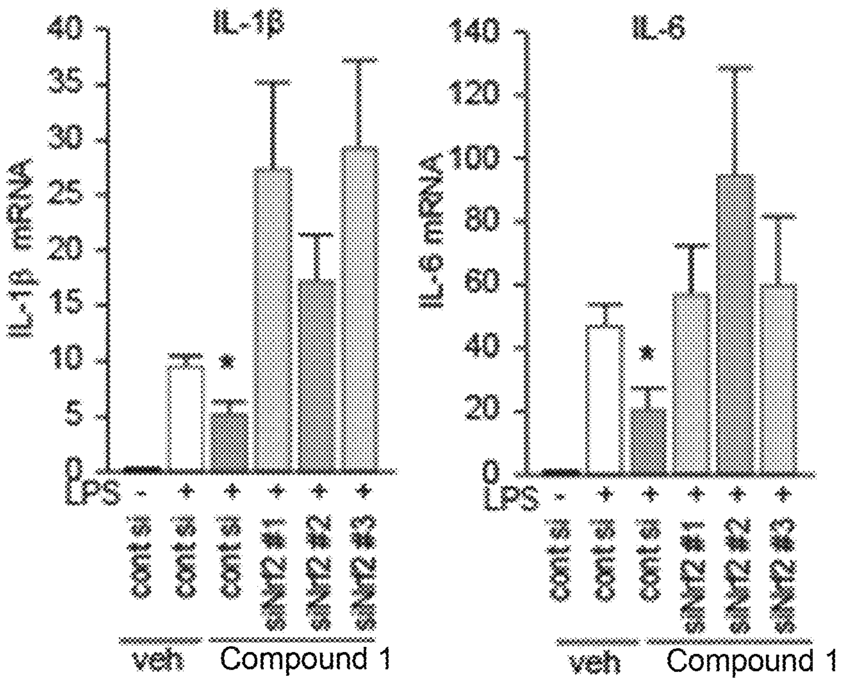

FIG. 2C shows results of qPCR analyses on the production of indicated cytokines in the presence or absence of Nrf2, with the treatment with the compound 1. In the cells treated with Nrf2 siRNA, the suppression of cytokine production was not observed. $^*P<0.05$.

These results indicate that the treatment with the compound 1 or 2 can suppress neuro-inflammation effectively.

In addition, these results explicitly indicate that the suppression of neuro-inflammation (suppression of cytokine production) by the compounds 1 and 2 was mediated through Nrf2.

Experiment Example 3: Effect of Enhancement of iPSC-Derived-Cell Transplantation Efficacy (In Vivo)

Dopaminergic neurons (DA neurons) were prepared from human iPSC and transplanted into murine brain to confirm that the treatment with the compound 2 enhanced the efficacy of the settlement of iPSC-derived DA neurons. The outlines are shown in FIGS. 3A to 3C.

Figure 3A:
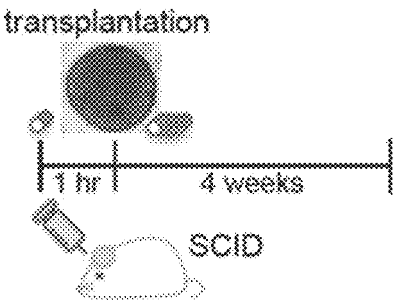
FIGS. 3A to 3C relate to the enhancement of efficacy of neuron transplantation.

FIG. 3A shows an experimental scheme. The compound 2 was administered to recipients (mice) one hour before the surgery of transplantation of the hiPSC-derived DA neurons. The drug administration was performed for four days consecutively till day 4 after the surgery when robust glial activation has been expected, and the animals were left without treatment for four weeks.

Figure 3B:
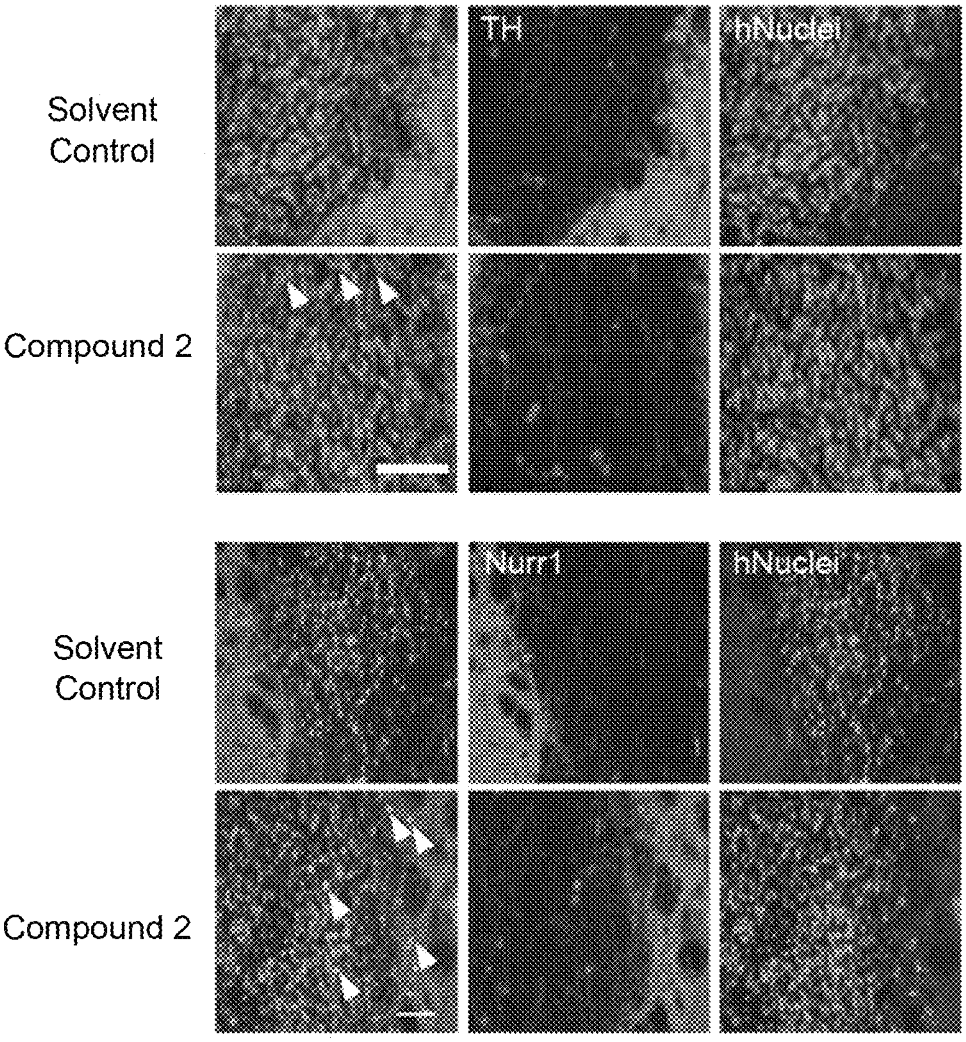

FIG. 3B shows representative images of cells transplanted in striatum tissues. Arrows indicate iPSC-derived cells that are co-labeled by TH or Nurr1 (both are dopaminergic markers). Scale bar=50 μm. The transplanted DA neurons were identified by hNuclei staining and survived iPSC-derived DA neurons were quantified with co-staining of TH and Nurr1 dopaminergic markers.

Figure 3C:
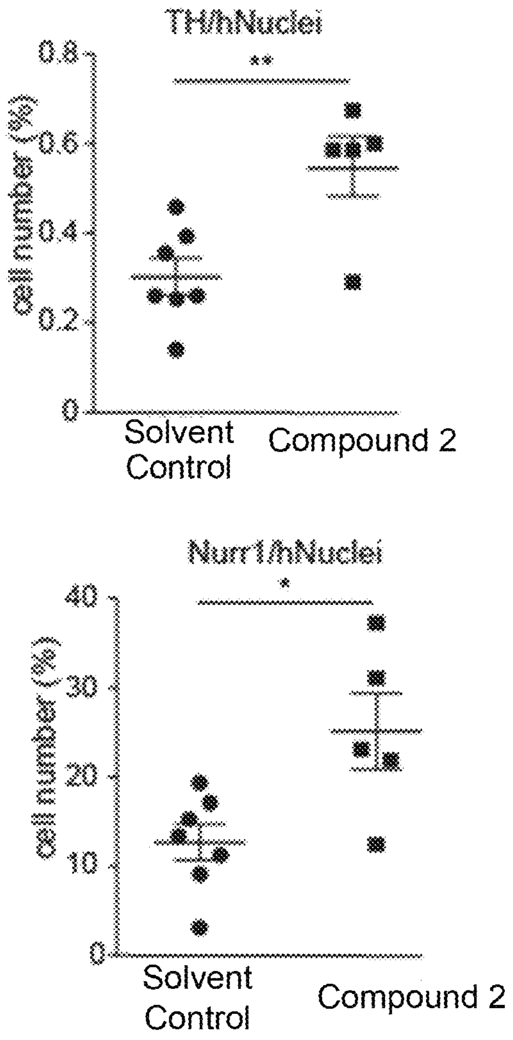

FIG. 3C shows results of quantitative analyses on transplanted cells. The number of double-positive cells of hNuclei and TH or Nurr1 was normalized to the number of hNuclei-positive cells. N=7 and N=5 under each condition. *$P<0.05$, **$P<0.01$.

The results shown in FIGS. 3A to 3C show that the treatment with the compound 2 improves the survival rate of iPSC-derived DA neurons four weeks after the transplantation.

Experiment Example 4: Effect of Suppressing Neurodegeneration Caused by Neuro-Inflammation (In Vivo)

It was confirmed that neurodegeneration caused by neuro-inflammation can be reduced by the compound 2. The outlines are shown in FIGS. 4A to 4F.

Figure 4A:
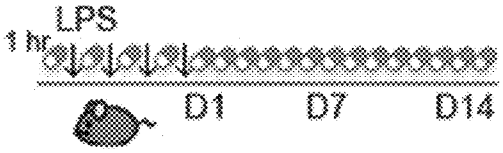
FIGS. 4A to 4F relate to the suppression of neurodegeneration caused by neuro-inflammation.

FIG. 4A shows an experimental scheme. LPS was intraperitoneally administered to mice to induce neuro-inflammation. Drug (the compound 2) was administered one hour before the LPS injection to the mice. The drug was orally administered at a indicated dose once daily.

Glial activation and cytokine production were evaluated at day 1 after the administration. Degeneration of dopaminergic nerves were evaluated at day 7 and day 14 (FIGS. 4B and 4C).

Figure 4B:
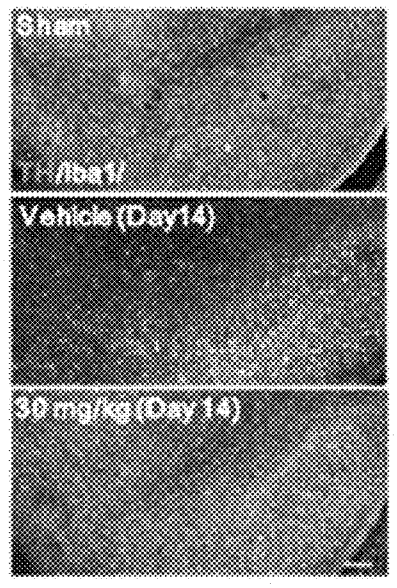

FIG. 4B shows representative images of substantia nigra of treated animals. TH (green), lba1 (gray scale), and GFAP (magenta) were used for markers of DA neurons, microglia, and astrocyte, respectively. Scale bar=200 μm.

Figure 4C:
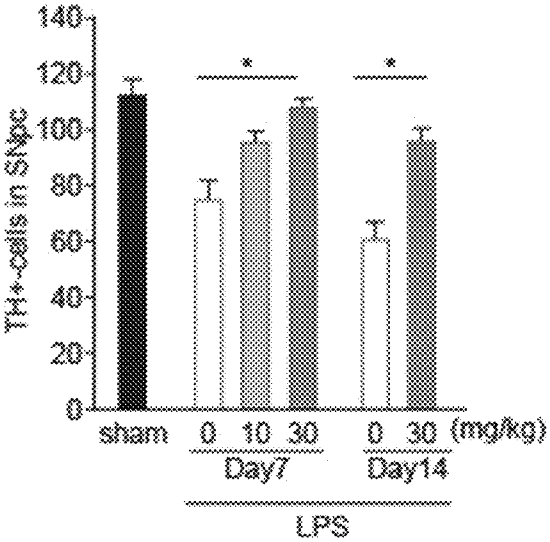

FIG. 4C shows results of quantification of the number of TH-positive cells in substantia nigra par compacta (SNpc). Animals, N=5 to 6, were analyzed regarding each condition. Error bars stand for SEM. *$P<0.05$.

It is confirmed that with the administration of the compound 2, the glial activation (FIG. 4D) and the cytokine production (FIGS. 4E and 4F) were suppressed.

Figure 4D:
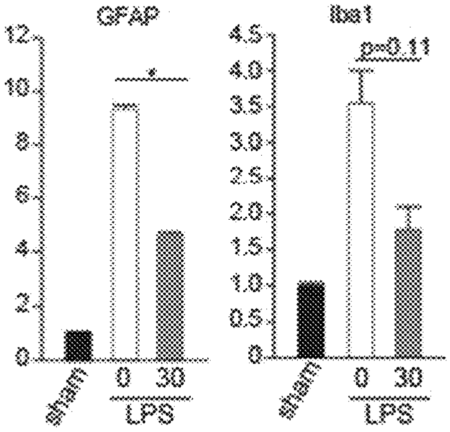

FIG. 4D shows results of quantitative analyses of glial activation by qPCR on striatum tissues at day 1 from last LPS injection. Error bars stand for SEM. *$P<0.05$.

Figure 4E:
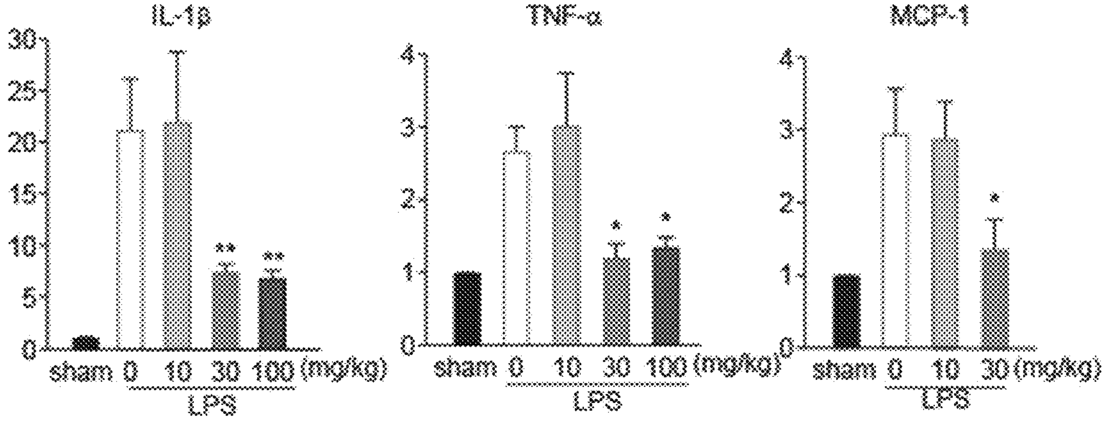
Figure 4F:
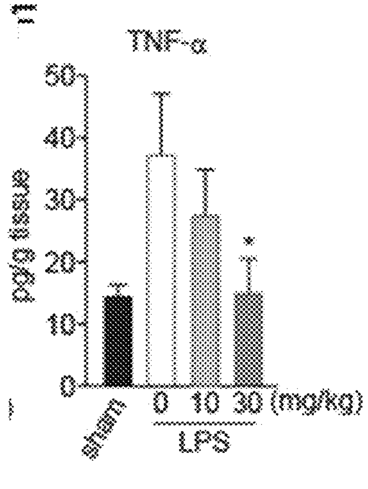

FIGS. 4E and 4F show results of analyses by qPCR (4E) and ELISA (4F) on the levels of indicated cytokines and chemokines from striatum tissues at day 1. Error bars stand for SEM. *$P<0.05$.

Importantly, the loss of dopaminergic neurons was rescued by the administration of the compound 2 (FIGS. 4B and 4C). In other words, neurodegeneration caused by neuro-inflammation can be reduced by the compound 2.

Experiment Example 5: Neuroprotective Mechanism Mediated Through Glial Cells (In Vitro)

With the compound 2, it was confirmed that a point of action of the neuroprotective function (effects of enhancing the effect of transplantation of iPS cells and suppressing cell degeneration caused by cell inflammation) is glial cells, as indicated by Experiment Examples 1 and 2.

To confirm that the protection of nerves is mediated through glial cells, a co-culture system was set up. hiPSC-derived dopaminergic neuron progenitors, and glial culture solution separated from embryonic day 13 murine brains were mixed and co-cultured. The mixed glial culture solution contained GFAP-positive and lba1-positive cells, but did not contain TH-positive cells.

Figure 5A:
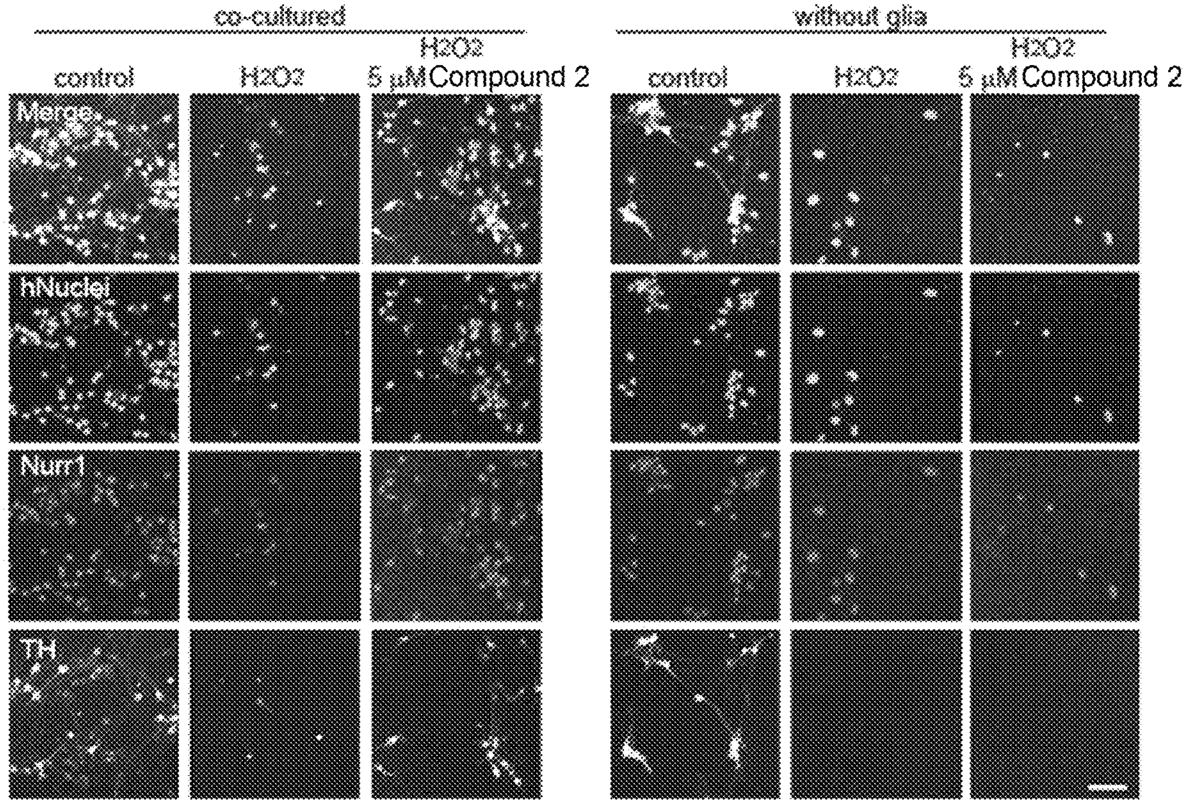
FIGS. 5A to 5C relate to a mechanism of neuroprotective function (effects of enhancing efficacy of transplantation of iPS-cell-derived neurons and suppressing cell degeneration caused by cell inflammation).
Figure 5B:
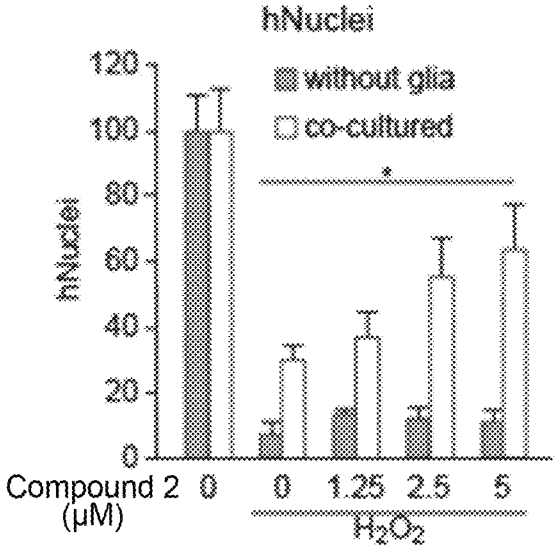
Figure 5C:
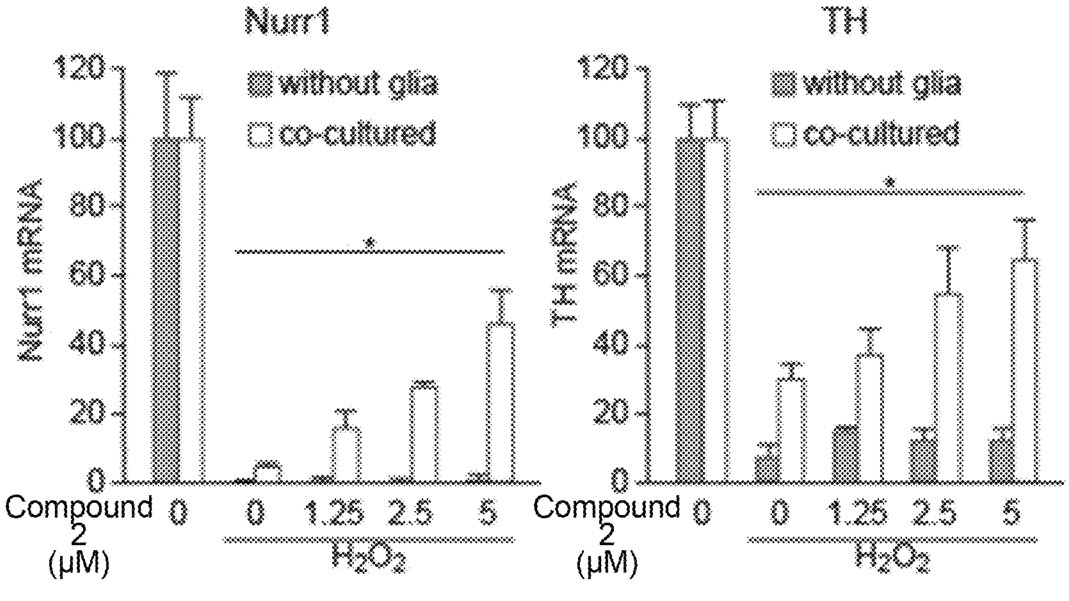

To the mixed glial culture solution, oxidative stress was induced by treatment with $H_2O_2$ (FIGS. 5A to 5C).

The neuronal survival was evaluated according to the number of human nuclei by immunostaining (FIGS. 5A and 5B).

Dopaminergic markers of Nurr1 and TH were evaluated by qPCR (FIG. 5C).

FIG. 5A shows representative images of hiPSC-derived dopaminergic neuron progenitors. hiPSC-derived DA neurons were visualized with anti-hNuclei (green), anti-Nurr1 (red), and anti-TH (gray scale) of antibodies. Scale bar=50 μm.

FIG. 5B shows quantitative analyses of the number of hNuclei. Data were normalized to the control condition without $H_2O_2$ treatment. *$P<0.05$.

FIG. 5C shows quantification by qPCR. Nurr1 and TH were used as markers of dopaminergic neurons in early differentiation and maturation respectively.

As shown in FIGS. 5A to 5C, the oxidative stress caused by the $H_2O_2$ treatment reduced the survival of DA neurons, but the survival amount increased depending on the added amount of the compound 2. The protection of neurons by the compound 2, however, did not occur without glia, and occurred only in the co-culture with glia.

These strongly indicate that the neuroprotective functions exerted by the compound 2 are mediated via glial cells.

What is claimed is:

1. A method for suppressing neuro-inflammation, comprising:

administering, to a subject, an effective amount of a pharmaceutical composition containing, as an active ingredient, a compound having an inhibiting ability against phosphorylation activity of DYRK1A protein, or a pharmaceutically acceptable salt of the compound, wherein the compound is a compound expressed by Formulae (I) or (II) shown below:

(I)

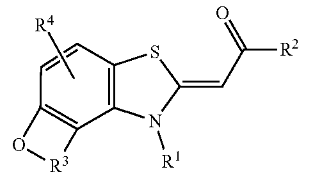

(II)

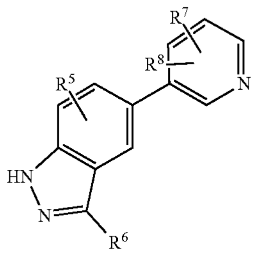

where, in Formula (I), $R^1$ represents a methyl group, an ethyl group, or a propyl group, $R^2$ represents a methyl group, $R^3$ represents $-CH_2-CH_2-$ or $-CH=CH-$, and $R^4$ represents a hydrogen atom, in Formula (II), $R^5$, $R^6$, $R^7$ and $R^8$ independently represent a hydrogen atom, a halogen atom, a carboxyl group, an amino group, a hydroxyl group, an alkyl group having 1 to 4 carbon atoms, or a halogen-atom-substituted alkyl group having 1 to 4 carbon atoms, and wherein the subject is a patient affected by disease selected from the group consisting of frontotemporal lobar degeneration, amyotrophic lateral sclerosis, and multiple sclerosis.

2. The method according to claim 1, wherein the compound is a compound expressed by either one of the following:

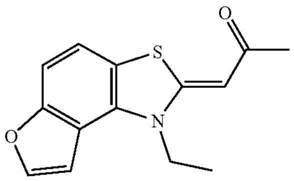 [SMILES: CCN1/C(=C/C(C)=O)Sc2ccc3occc3c21]

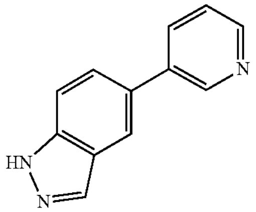

3. The method according to claim 1, wherein the compound is a compound expressed by:

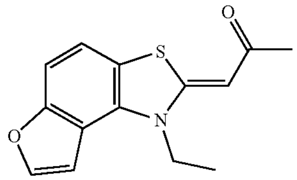

4. The method according to claim 1, comprising orally administrating the pharmaceutical composition.

5. A method for protecting a nerve cell from neuro-inflammation by promoting the stabilization of Nrf2 protein in glial cells, comprising:

administering, to a subject, an effective amount of a pharmaceutical composition containing, as an active ingredient, a compound having an inhibiting ability against phosphorylation activity of DYRK1A protein, or a pharmaceutically acceptable salt of the compound, wherein the compound is a compound expressed by Formulae (I) or (II) shown below:

(I)

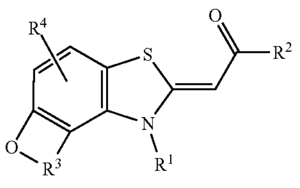

-continued (II)

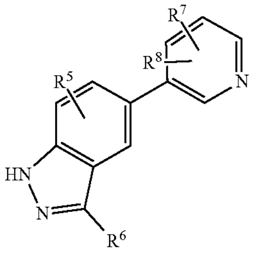

where, in Formula (I), $R^1$ represents a methyl group, an ethyl group, or a propyl group, $R^2$ represents a methyl group, $R^3$ represents $-CH_2-CH_2-$ or $-CH=CH-$, and $R^4$ represents a hydrogen atom, in Formula (II), $R^5$, $R^6$, $R^7$ and $R^8$ independently represent a hydrogen atom, a halogen atom, a carboxyl group, an amino group, a hydroxyl group, an alkyl group having 1 to 4 carbon atoms, or a halogen-atom-substituted alkyl group having 1 to 4 carbon atoms, and wherein the subject is a patient affected by disease selected from the group consisting of frontotemporal lobar degeneration, amyotrophic lateral sclerosis, and multiple sclerosis.

6. The method according to claim 5, wherein the compound is a compound expressed by either one of the following:

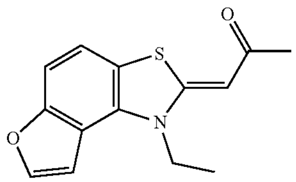 [SMILES: CCN1/C(=C/C(C)=O)Sc2ccc3occc3c21]

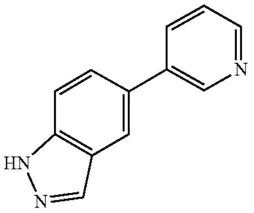

7. The method according to claim 5, wherein the compound is a compound expressed by:

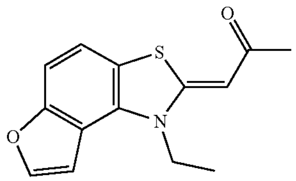 [SMILES: CCN1/C(=C/C(C)=O)Sc2ccc3occc3c21]

8. The method according to claim 5, comprising orally administrating the pharmaceutical composition.

9. A method for increasing a post-transplantation settlement rate of a transplanted cell, comprising:

administering, to a recipient, an effective amount of a pharmaceutical composition, before, simultaneously with, or after transplantation of a cell, wherein the cell is selected from the group consisting of neuron precursor cell, pluripotent stem cell, and neuron, the pharmaceutical composition contains, as an active ingredient, a compound having an inhibiting ability against phosphorylation activity of DYRK1A protein, or a pharmaceutically acceptable salt of the compound, and the compound is a compound expressed by Formulae (I) or (II) shown below:

(I)

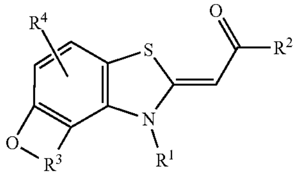

(II)

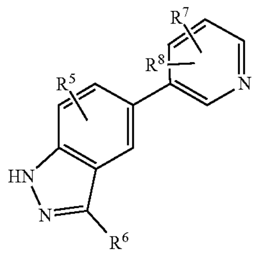

where, in Formula (I), $R^1$ represents a methyl group, an ethyl group, or a propyl group, $R^2$ represents a methyl group, $R^3$ represents $-CH_2-CH_2-$ or $-CH=CH-$, and $R^4$ represents a hydrogen atom, in Formula (II), $R^5$, $R^6$, $R^7$ and $R^8$ independently represent a hydrogen atom, a halogen atom, a carboxyl group, an amino group, a hydroxyl group, an alkyl group having 1 to 4 carbon atoms, or a halogen-atom-substituted alkyl group having 1 to 4 carbon atoms, and wherein the recipient is a patient in need of or receiving the transplantation of the cell, and the patient is affected by a neurodegenerative disease selected from the group consisting of infarction of spinal cord, limb paralysis, Parkinson's disease, and Huntington's disease.

10. The method according to claim 9, wherein the compound is a compound expressed by either one of the following:

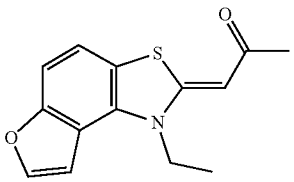

-continued

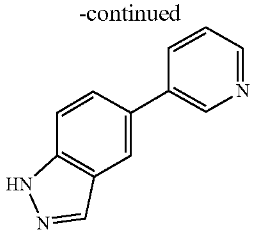

11. The method according to claim 9, wherein the compound is a compound expressed by:

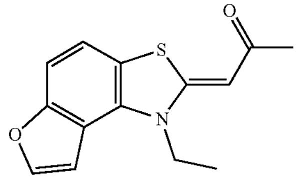

12. A method for increasing a post-transplantation survival rate and/or a post-transplantation retention rate of a transplanted cell, comprising:

administering, to a recipient, an effective amount of a pharmaceutical composition, before, simultaneously with, or after transplantation of a cell, wherein the cell is selected from the group consisting of neuron precursor cell, pluripotent stem cell, and neuron, the pharmaceutical composition contains, as an active ingredient, a compound having an inhibiting ability against phosphorylation activity of DYRK1A protein, or a pharmaceutically acceptable salt of the compound, and the compound is a compound expressed by Formulae (I) or (II) shown below:

(I)

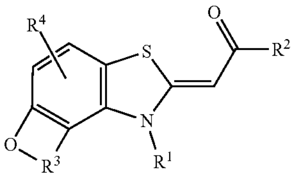

(II)

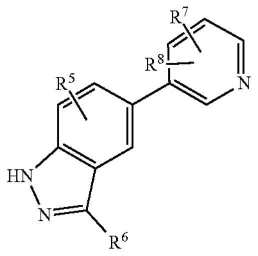

where, in Formula (I), $R^1$ represents a methyl group, an ethyl group, or a propyl group, $R^2$ represents a methyl group, $R^3$ represents $-CH_2-CH_2-$ or $-CH=CH-$, and $R^4$ represents a hydrogen atom, in Formula (II), $R^5$, $R^6$, $R^7$ and $R^8$ independently represent a hydrogen atom, a halogen atom, a carboxyl group, an amino group, a hydroxyl group, an alkyl group having 1 to 4 carbon atoms, or a halogen-atom-substituted alkyl group having 1 to 4 carbon atoms, and wherein the recipient is a patient in need of or receiving the transplantation of the cell, and the patient is affected by a neurodegenerative disease selected from the group consisting of infarction of spinal cord, limb paralysis, Parkinson's disease, and Huntington's disease.

13. The method according to claim 12, wherein the compound is a compound expressed by either one of the following:

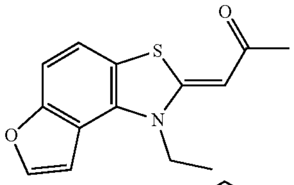

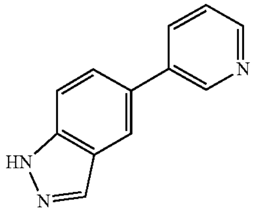

14. The method according to claim 12, wherein the compound is a compound expressed by:

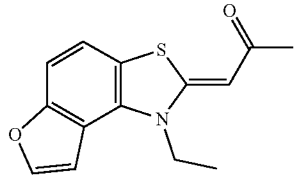

15. The method according to claim 9, comprising administering, to the recipient, an effective amount of a pharmaceutical composition, before and after the transplantation.

16. The method according to claim 9, wherein the neurodegenerative disease is selected from the group consisting of Parkinson's disease and Huntington's disease.

17. The method according to claim 12, comprising administering, to the recipient, an effective amount of a pharmaceutical composition, before and after the transplantation.

18. The method according to claim 12, wherein the neurodenerative disease is selected from the group consisting of Parkinson's disease and Huntington's disease.

* * * * *